US00PP30251P2

(12) United States Plant Patent
Van Swieten

(10) Patent No.: US PP30,251 P2
(45) Date of Patent: Feb. 26, 2019

(54) ***PHALAENOPSIS* ORCHID PLANT NAMED 'PHALFATYK'**

(50) Latin Name: ***Phalaenopsis* hybrid**
Varietal Denomination: PHALFATYK

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/732,640

(22) Filed: Dec. 7, 2017

(51) Int. Cl.
*A01H 6/62* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALFATYK', particularly characterized by having small, white flowers with a purple center, 1 to 3 peduncles that are short and moderate, leaves that are oblong, and is propagated by meristem tissue culture, is disclosed.

3 Drawing Sheets

Genus and species: *Phalaenopsis* hybrid.
Variety denomination: 'PHALFATYK'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFATYK'.

The new *Phalaenopsis* plant is a product of a planned breeding program conducted by the inventor in Bleiswijk, The Netherlands. The objective of this breeding program was to create a new *Phalaenopsis* plant with numerous small, attractive and unique white flowers with purple center, suitable for potted plant production.

The new *Phalaenopsis* plant 'PHALFATYK' is a result of cross-pollination made by the inventor in December 2007 in Bleiswijk, The Netherlands of the proprietary female, or seed parent, *Phalaenopsis* hybrid '01-1789' (unpatented) with the proprietary male, or pollen parent, *Phalaenopsis* hybrid 'PHALDOMEO' (U.S. Plant Pat. No. 25,682).

The new *Phalaenopsis* was selected by the inventor as a single plant within the progeny of the stated cross-pollination in a controlled greenhouse in Bleiswijk, The Netherlands in December 2010. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALFATYK' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFATYK' as a new and distinct variety of *Phalaenopsis* plant.

1) Small, white flowers with a purple center;
2) 1 to 3 peduncles;
3) Peduncle is short and moderate; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 40-week old plants in October 2017. Colors in the photographs may differ from the color values cited in the detailed botanical description, which accurately describe the actual colors of the new variety.

DESCRIPTION OF THE NEW VARIETY

Figure 1:
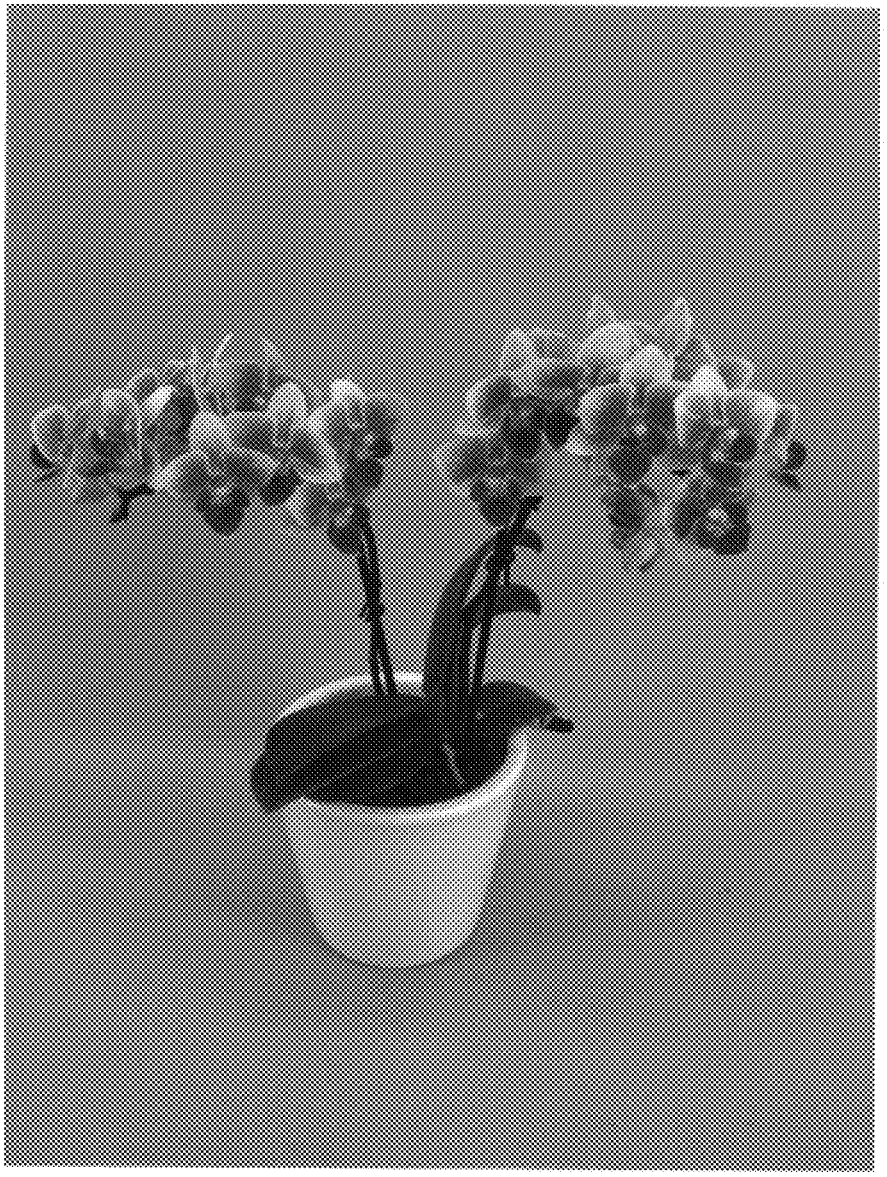
FIG. 1 shows the overall plant habit, including blooms and foliage of 'PHALFATYK'.
Figure 2:
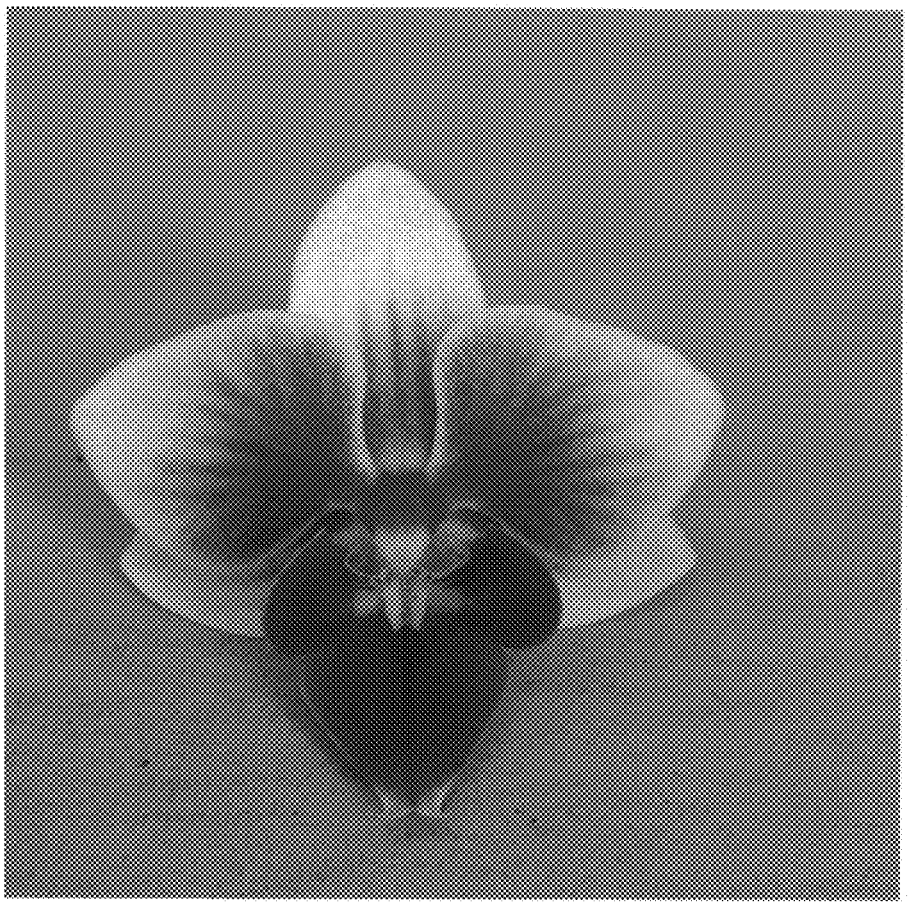
FIG. 2 shows a close-up of a flower of 'PHALFATYK'.
Figure 3:
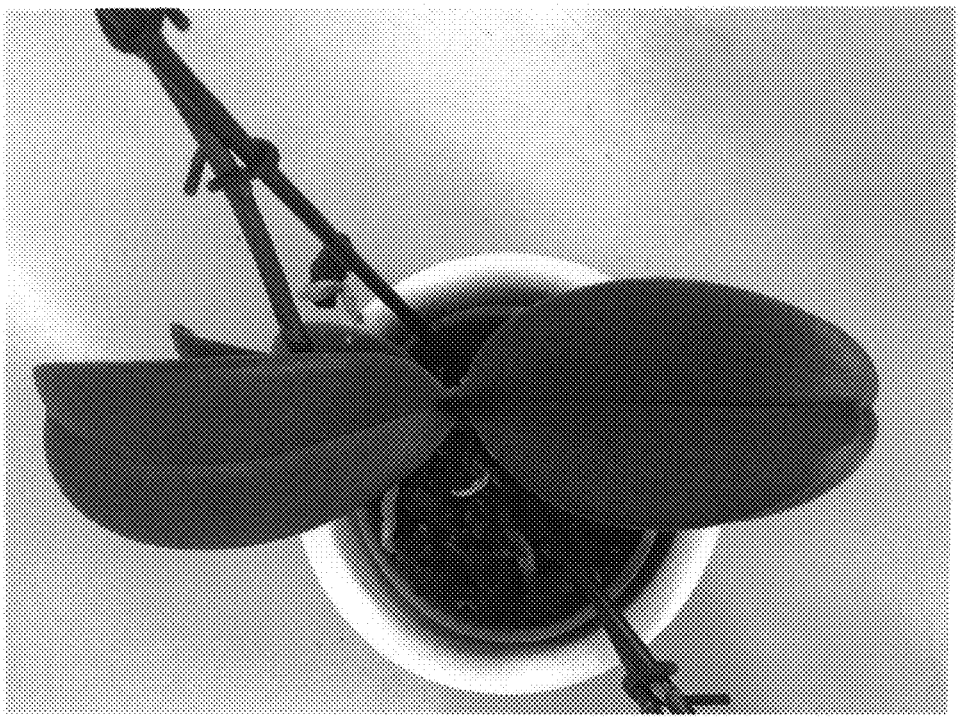
FIG. 3 shows a close-up of the leaves of 'PHALFATYK'.

The following detailed description sets forth the distinctive characteristics of 'PHALFATYK'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in October 2017 on 40-week old plants which were planted from a nursery tray in 9 centimeter (diameter) pots and grown in a greenhouse between 27° C. to 29° C. for 20 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFATYK'.

Parentage:

*Female parent*.—*Phalaenopsis* cultivar '01-1789' (unpatented).

*Male parent*.—*Phalaenopsis* cultivar 'PHALDOMEO' (U.S. Plant Pat. No. 25,682).

Propagation:

*Type*.—Meristem tissue culture.

Roots:

*Root description*.—Greyed-green colored roots (RHS 190B/C) with branching lateral roots having light green colored root tips (RHS 144B/C).

Plant:

*Commercial crop time to flowering*.—Following asexual propagation (in-vitro), the rooted cutting grows for 20 to 24 weeks and is transplanted to a 9 cm pot. The plants are finished after 38-40 weeks.

*Growth habit of peduncle*.—Standard, green leaves, raceme to panicle.

*Height* (*from soil level to top of inflorescence*).—Approximately 30.0 cm to 35.0 cm.

*Width* (*measured from leaf tips*).—About 20.0 cm to 23.0 cm.

*Vigor*.—Moderate.

Leaves:

*Mature leaves*.—Quantity per plant: 7 to 9 leaves are produced before flowering. Length (fully expanded): 10.0 cm to 12.0 cm. Width: 5.5 cm to 6.5 cm. Shape: Oblong. Base shape: Slightly elongated. Apex: Obtuse unequal. Leaf blade angle with the petiole (measured from the horizontal position): Between 15 degrees and 30 degrees. Leaf margin: Entire. Color: Upper surface: RHS 146A. Lower surface: RHS 146B. Texture: Rough. Thickness: 2.2 mm to 2.4 mm. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—17 to 25.

*Length*.—30.0 cm to 35.0 cm.

*Diameter*.—4.1 mm to 4.5 mm.

*Strength*.—Moderate.

*Aspect*.—Upright to slightly pendant.

*Texture*.—Smooth.

*Color*.—Brown (RHS 200B).

*Internode length*.—3.0 cm to 4.0 cm.

*Callosities*.—None.

Inflorescence description:

*Appearance*.—Upright to slightly pendant, raceme to panicle inflorescence with twisted (non-bilaterally) symmetrical flowers that open in succession beginning with the lowermost flower.

*Inflorescence size*.—Height (from base to tip): 140.0 mm to 190.0 mm.

*Flowering time*.—First flowers can be expected 7 to 8 months after planting in a 9 cm (diameter) pot.

*Flower*.—Height: 38.0 mm to 43.0 mm. Diameter: 42.0 mm to 47.0 mm. Depth of lip: 16.0 mm to 18.0 mm.

*Flower longevity*.—On the plant: 8 to 13 weeks.

*Fragrance*.—Absent.

*Flower bud*.—Average size: Medium. Length: 14.0 mm to 16.0 mm. Width: 12.0 mm to 14.0 mm. Shape: Egg shaped. Color: Mix of light green (RHS 145C/D) with a touch of red-purple (RHS 72A/B).

*Petals*.—Arrangement: Open/free. Shape: Semi-circular. Apex: Obtuse symmetric. Margin: Entire. Length (from base to tip): 20.0 mm to 22.0 mm. Width: 21.0 mm to 23.0 mm. Color (when fully opened): Upper surface: Basic color: White (RHS NN155C). Over color: Purple (RHS N78B). Lower surface: Basic color: Purple (RHS N78C/D). Over color: White (RHS NN155C).

*Dorsal sepal*.—Shape: Elliptic. Apex: Obtuse symmetric. Margin: Entire. Length (from base to tip): 24.0 mm to 26.0 mm. Width: 15.0 mm to 17.0 mm. Color (when fully opened): Upper surface: Basic color: White (RHS NN155C). Over color: Purple (RHS N78B). Lower surface: Basic color: White (RHS NN155C). Over color: Light purple (RHS N78D).

*Lateral sepals*.—Shape: Ovate. Apex: Obtuse. Margin: Entire. Length (from base to tip): 23.0 mm to 25.0 mm. Width: 15.0 mm to 17.0 mm. Color (when fully opened): Upper surface: Basic color: White (RHS NN155C). Over color: Purple (RHS N78B). Lower surface: Basic color: White (RHS NN155C). Over color: Touch of light purple (RHS N78D).

*Labellum* (*lip*).—Whiskers: Present. Length of whiskers: 1.0 mm to 2.0 mm. Color of whiskers: White (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 13.0 mm to 15.0 mm. Width: 8.0 mm to 10.0 mm. Color: Yellow (RHS 7B) at the base; purple (RHS N78A) toward the margin.

*Apical lobe*.—Shape: Ovate. Margin: Entire. Length: 15.0 mm to 17.0 mm. Width: 14.0 mm to 16.0 mm. Color: Slightly yellow (RHS 7C) at the base; purple (RHS N78A) toward the whiskers.

*Callus*.—Average size: Small. Height: 3.0 mm to 4.0 mm. Length: 3.0 mm to 4.0 mm. Width: 3.0 mm to 4.0 mm. Color: Light yellow (RHS 10C/D) with very small dots.

Reproductive organs:

*Column*.—Length: 8.0 mm to 10.0 mm. Diameter: 3.5 mm to 3.7 mm. Color: Purple (RHS N78B).

*Pollinia*.—Quantity: 2. Diameter: 0.7 mm to 0.9 mm. Color: Orange (RHS 24A).

*Ovary*.—Length: 6.0 mm to 8.0 mm. Diameter: 1.5 mm to 1.7 mm.

*Pedicel*.—Length: 29.0 mm to 31.0 mm. Diameter: 1.8 mm to 2.0 mm. Color: Light green (RHS 144B/C) and very light green (RHS 157D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALFATYK', cultivar '01-1789' (unpatented), is no longer in existence, so a meaningful comparison cannot be made.

'PHALFATYK' differs from male parent plant 'PHALDOMEO' (U.S. Plant Pat. No. 25,682) in that 'PHALFATYK' has petals with purple (RHS N78B) over color and a light yellow callus, whereas 'PHALDOMEO' has petals with purple (RHS N78A) over color and a yellow callus. Additionally, 'PHALFATYK' has larger flowers and longer leaves than 'PHALDOMEO'.

'PHALFATYK' is most similar to the commercial *Phalaenopsis* plants named 'PHALELENO' (unpatented) and 'PHALDONFI' (U.S. Plant Pat. No. 26,066). 'PHALFATYK' differs from the commercial variety 'PHALELENO' in that 'PHALFATYK' has brown peduncles and an apical lobe that is slightly yellow at the base with purple toward the whiskers, whereas 'PHALELENO' has green peduncles with a touch of brown and an apical lobe that is red with yellow on the sides and purple toward the whiskers. Additionally, 'PHALFATYK' has narrower apical lobes than 'PHALELENO'.

'PHALFATYK' differs from the commercial variety 'PHALDONFI' in that 'PHALFATYK' has a center flower pattern, a weakly spatulate lateral lobe and an apical lobe that is slightly yellow at the base with purple toward the whiskers, whereas 'PHALFDONFI' has a striped flower pattern, a spatulate lateral lobe and a red-purple apical lobe. Additionally, 'PHALFATYK' has narrower apical lobes than 'PHALDONFI'.

I claim:

1. A new and distinct variety of *Phalaenopsis* plant named 'PHALFATYK', substantially as described and illustrated herein.

* * * * *